United States Patent [19]

Carden

[11] Patent Number: 5,722,033
[45] Date of Patent: Feb. 24, 1998

[54] FABRICATION METHODS FOR METAL MATRIX COMPOSITES

[75] Inventor: Robin A. Carden, Costa Mesa, Calif.

[73] Assignee: Alyn Corporation, Irvine, Calif.

[21] Appl. No.: 674,166

[22] Filed: Jul. 1, 1996

Related U.S. Application Data

[60] Continuation of PCT/US96/06176, May 2, 1996, which is a continuation-in-part of Ser. No. 536,695, Sep. 29, 1995, which is a division of Ser. No. 183,728, Jan. 19, 1994, Pat. No. 5,486,223.

[51] Int. Cl.$^6$ .............. B22F 3/12; C22C 1/05; C22C 1/03; C22C 21/00

[52] U.S. Cl. .............. 419/12; 419/28; 419/29; 419/41; 419/54; 419/55; 164/47; 164/66.1; 164/DIG. 6; 164/DIG. 7; 29/DIG. 31

[58] Field of Search .............. 419/5, 12, 28, 419/29, 41, 54, 55; 164/47, 66.1, DIG. 6, DIG. 7; 29/DIG. 31

[56] References Cited

U.S. PATENT DOCUMENTS

| | | |
|---|---|---|
| 3,178,807 | 4/1965 | Bergmann . |
| 3,591,362 | 7/1971 | Benjamin . |
| 4,104,062 | 8/1978 | Weaver . |
| 4,605,440 | 8/1986 | Halverson et al. . |
| 4,623,388 | 11/1986 | Jatkar et al. . |
| 4,661,154 | 4/1987 | Faure . |
| 4,702,770 | 10/1987 | Pyzik et al. . |
| 4,749,545 | 6/1988 | Begg et al. . |
| 4,786,467 | 11/1988 | Skibo et al. .............. 420/129 |
| 4,793,967 | 12/1988 | Pryor et al. . |
| 4,865,806 | 9/1989 | Skibo et al. .............. 420/129 |
| 4,894,088 | 1/1990 | Yamaguchi et al. . |
| 4,941,918 | 7/1990 | Horikoshi et al. . |
| 4,943,320 | 7/1990 | Pechnik et al. . |
| 4,946,500 | 8/1990 | Zedalis et al. . |
| 4,961,778 | 10/1990 | Pyzik et al. . |
| 4,981,643 | 1/1991 | Siemers et al. . |
| 5,006,417 | 4/1991 | Jackson et al. . |
| 5,034,282 | 7/1991 | Hribernik et al. . |
| 5,039,633 | 8/1991 | Pyzik et al. . |
| 5,045,278 | 9/1991 | Das et al. . |
| 5,114,505 | 5/1992 | Mirchandani et al. . |
| 5,128,213 | 7/1992 | Tanaka et al. . |
| 5,167,920 | 12/1992 | Skibo et al. .............. 420/548 |
| 5,273,569 | 12/1993 | Gilman et al. . |
| 5,372,775 | 12/1994 | Hayashi et al. . |
| 5,401,338 | 3/1995 | Lin . |
| 5,435,825 | 7/1995 | Kusui et al. . |

OTHER PUBLICATIONS

"Powder Techniques in Processing of Metal Matrix Composites" by H.J. Rack in Metal Matrix Composites: Processing and Interfaces edited by R. K. Everett and R.J. Arsenault, Academic Press, 1991, pp. 83–101.

*Primary Examiner*—Daniel J. Jenkins
*Attorney, Agent, or Firm*—Cooper & Dunham LLP

[57] ABSTRACT

A method of extruding a boron carbide-aluminum alloy metal matrix composite includes heating the ingots of the composite to temperatures of about 570° C., holding the ingots at about 570° C. to soften the ingots, placing the ingots in a heated extrusion chamber, and extruding the softened ingots at pressures about 15% to 20% higher than typical pressures used to extrude aluminum alloys. A method of casting a boron carbide-aluminum alloy metal matrix composite includes heating ingots of the composite to about 700° C. to melt the ingots, gently stirring the melt, removing dross from the melt, vigorously stirring the melt with an impeller without creating a vortex, degassing the melt with an argon diffuser wand, and continuously removing froth formed during degassing until the rate of froth formation is reduced and the melt gently bubbles.

14 Claims, 5 Drawing Sheets

FABRICATION METHODS FOR METAL MATRIX COMPOSITES

CROSS-REFERENCE TO RELATED APPLICATIONS

This is a continuation-in-part of application Ser. No. 08/536,695 filed Sep. 29, 1995 now allowed which, in turn, is a division of application Ser. No. 08/183,728, Jan. 19, 1994 now U.S. Pat. No. 5,486,223. This application is entitled to the benefits under 35 U.S.C. §120 of International Application PCT/US96/06176 filed May 2, 1996.

BACKGROUND

The present invention relates generally to metal matrix compositions. Such compositions or composites comprise a metal matrix material such as aluminum, titanium, magnesium, or alloys thereof, for example, to which is added a selected percentage of ceramic material to improve properties such as strength, hardness, and drawability of the metal matrix material. Drawability facilitates fabrication of various articles of manufacture from such metal matrix composites. More specifically, the present invention pertains to an improved metal matrix composite which, in a preferred embodiment, uses boron carbide as the added ceramic material. The composites result from a novel method of manufacture producing a material that is lighter, stronger, stiffer, and has a higher fatigue strength than other available alloys of the metal matrix material, and that is also lighter, stronger, stiffer, and has a higher fatigue strength than prior art metal matrix composites, particularly those metal matrix composites which are of comparable cost.

In recent years metal matrix composites have become popular materials for a variety of applications because of improvements in stiffness, strength, and wear properties. Basic metal matrix composites typically are made with aluminum, titanium, or magnesium as the metal matrix material to which is added certain percentages of ceramic material. Typical ceramic additives include boron carbide, silicon carbide, titanium diboride, titanium carbide, aluminum oxide, and silicon nitride. Most known metal matrix composites are made by introducing the ceramics into molten metal matrix material. In order for the improved properties to be realized, the molten metal must wet the ceramic material so that clumping of the ceramic material is minimized. Numerous schemes with varying degrees of success have been utilized to improve the dispersion of the ceramic material in the molten metal.

Recently, powder metallurgy consolidation has emerged as an attractive alternative method for fabricating metal matrix composites, where powders are compacted by means of hot pressing and vacuum sintering to achieve a high density ingot. By following certain pressing and sintering techniques, an ingot of 99% theoretical density can be achieved.

One problem encountered in metal matrix composites of aluminum and silicon carbide is the thermodynamic instability of silicon carbide in molten aluminum. This instability leads to the formation of aluminum carbide precipitates at grain boundary interfaces and an increased concentration of silicon in the metal matrix during solidification from the molten state, and these occurrences are believed to have detrimental effects on the mechanical properties of the resulting composite.

An alternative and superior ceramic material for metal matrix composites is boron carbide. Boron carbide is the third hardest material known and the hardest material produced in tonnage. Boron carbide is also the lightest of the ceramic materials, and therefore may be used to improve the mechanical properties of metal matrix composites without increasing the weight of the composites.

Boron carbide powders can be formed by a variety of reactions including the carbon reduction of any of several boron-oxygen compounds including boric oxide, borax, boracite, as well as by the direct combination of the elements. Usually, most commercial boron carbide is produced in an arc furnace. Boric acid is added together with carbon in the form of coke and heated to very high temperatures. An electric arc is maintained between graphite electrodes inside the furnace. The synthesis reaction is accompanied by the release of a large volume of carbon monoxide gas, and venting and disposal of this carbon monoxide gas constitutes a major concern in boron carbide production.

One consideration in working with boron carbide-metal matrix composites is that the high hardness of the boron carbide may limit the extrudability of the composites. It would be highly advantageous to produce an improved metal matrix composite that utilizes an advanced ceramic such as boron carbide and which is extrudable and can easily be fabricated into various articles of manufacture that exhibit superior strength and stiffness characteristics compared with equivalent articles of manufacture made of only the metal matrix material.

OBJECTS AND SUMMARY OF THE INVENTION

In view of the aforementioned considerations, it is an object of the present invention to provide a boron carbide-metal matrix composite that exhibits certain advantageous properties and manufacturability conducive to the fabrication of articles of manufacture having improved characteristics such as reduced weight, higher strength, and increased hardness.

It is another object of the present invention to provide fabrication methods such as casting and extrusion for producing articles of manufacture made of boron carbide-metal matrix composites.

According to an aspect of the present invention, an improved metal matrix composite that contains boron carbide ceramic additives is produced by a method unlike those for other metal matrix composites because the improved metal matrix composite of the present invention is not made through molten metal processes. More specifically, instead of adding the boron carbide to molten aluminum, nickel, zinc, magnesium, titanium, or other metal matrix material, the metal matrix composite of the present invention is made by blending together dry powders of the metal matrix material and the boron carbide to produce a homogeneous mixture. After the powders have been sufficiently mixed, they are subjected to high pressures and heat to transform the powders into solid ingots of a boron carbide-metal matrix composite. These ingots are then used in casting and extrusion operations to produce articles of manufacture made of such a composite. These composites can be approximately 60% lighter, 30% stronger, 45% stiffer, and 50% higher in fatigue strength than any of the 7000-series aluminum alloy materials. In addition, these composites can be approximately 8% lighter, 26% stronger, 5% stiffer, and have 40% greater fatigue strength than most other metal matrix composites available. Further, boron carbide-aluminum alloy metal matrix composites can exhibit a tensile strength of about 50 to 105 kpsi and a yield strength of about 45 to 100 kpsi. Furthermore, these composites can be approximately as hard as chromoly steel but have a density that is lower than that of aluminum or its alloys.

According to another aspect of the present invention, solid ingots of a boron carbide-metal matrix composite can be cast into articles of various shape by melting the ingots of the metal matrix composite in a crucible, gently stirring the molten material, skimming off and discarding any surface dross that forms, agitating the molten material with an impeller, degassing the molten material with an argon diffuser wand, and skimming off and discarding any surface froth that forms. The molten material is ready to be cast after the rate of froth formation is reduced and the molten material gently bubbles around the diffuser wand.

According to yet another aspect of the present invention, solid ingots of boron carbide-aluminum alloy metal matrix composite can be extruded by heating the ingots to soften the composite without melting it, transferring the softened composite to an extrusion chamber held at a temperature below the softening temperature, and extruding the softened composite at a pressure about 15% to 20% greater than that used for extruding aluminum alloys such that the average exit speed is about 15 to 30 feet/minute and the exit temperature is about 10° C. cooler than the temperature of the extrusion chamber.

Certain compositions of these composites are also readily weldable. In fact, coated boron carbide particulates tend to flux and move into the weld pool to create a very strong weld joint. Boron carbide has a melting temperature of about 2450° C. and is chemically inert at aluminum alloy processing temperatures. Thus, the present invention is not only highly suited for the manufacture of articles of various shapes, but is also suited for interconnecting such articles by conventional welding processes.

DETAILED DESCRIPTION OF PREFERRED EMBODIMENTS

Figure 1:
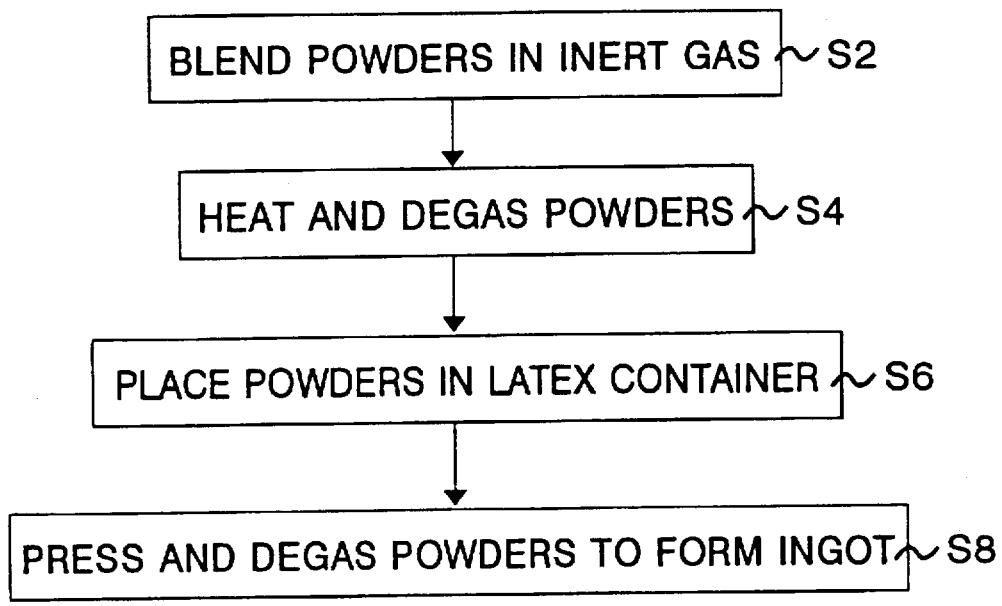
FIG. 1 is a flow chart describing a process of consolidating the powder constituents of the composite according to an embodiment of the present invention.

Preferred embodiments of the present invention are described below with reference to the accompanying drawings, in which like reference numerals represent the same or similar elements.

In an embodiment of the present invention, a metal matrix composite is comprised of boron carbide ceramic material and aluminum or aluminum alloy metal matrix material, wherein the aluminum or aluminum alloy metal matrix material has a purity of approximately 97% when in powder form. The balance of the metal matrix material may contain trace amounts of various elements such as chromium, copper, iron, magnesium, silicon, titanium, and zinc. The boron carbide powder used in forming the composite has a purity of 99.5% and a particulate size typically in the range of 2 to 19 µm with an average particulate size of approximately 5 to 8 µm. The boron carbide can be characterized as $B_4C$ and is comprised of approximately 77% boron and 22% carbon.

The composite is formed by blending the metal matrix powder material with the boron carbide powder. Included in the boron carbide powder is approximately 0.2 to 0.8 weight % silicon, 0.1 to 0.8 weight % iron, and 0.1 to 0.8 weight % aluminum, which are added to improve the boron carbide for use in the metal matrix composite. These elements are usually present in an amount less than about 6% by weight and do not go out of solution but instead remain with the boron carbide during subsequent processing of the metal matrix composite. These additives improve the chelating properties of the metal matrix material by forming intermetallic bonds with the metal matrix material. Trace amounts of magnesium, titanium, and calcium may also be included with the additives.

Two exemplary semi-quantitative analyses of acceptable boron carbide powders for use in the present invention are shown hereinbelow in Tables I and II. However, it will be understood that the aforementioned additions of pure aluminum, silicon, and iron, may not be the only metals that can be used for the stated purpose. By way of example, virtually any low temperature metal that forms an intermetallic phase without melting the metal matrix material could be used in the present invention for the purpose indicated.

TABLE I

| B | 77.3% |
|---|---|
| Si | 0.37 |
| Mg | 0.0016 |
| Fe | 0.026 |
| Al | 0.18 |
| Cu | 0.0021 |
| Ti | 0.0088 |
| Ca | 0.0049 |
| other elements | (nil) |
| C, $O_2$ | (bal) |

TABLE II

| B | 77.7% |
|---|---|
| Si | 0.14 |
| Mg | 0.0017 |
| Fe | 0.074 |
| Al | 0.13 |
| Cu | ND 0.0002 |
| Ti | 0.017 |
| Ca | 0.0048 |
| other elements | (nil) |
| C, $O_2$ | (bal) |

As described in the flow chart of FIG. 1, after the boron carbide powder and the aluminum or aluminum alloy powder are blended together for about 2.5 hours at 20 to 30 rpm in an inert gas at step S2, the powders are degassed at 200° C. for about 1 hour in a vacuum of approximately 5 to 8 Torr at step S4 and then placed in a latex bag at step S6 and isostatically pressed at 65,000 psi. The latex bag is degassed and clamped off, and the pressure is held at this value for at least 1 minute at step S8. The resulting ingots are then removed from the bag and placed into a vacuum furnace to undergo a sintering cycle, as described immediately below.

Figure 2:
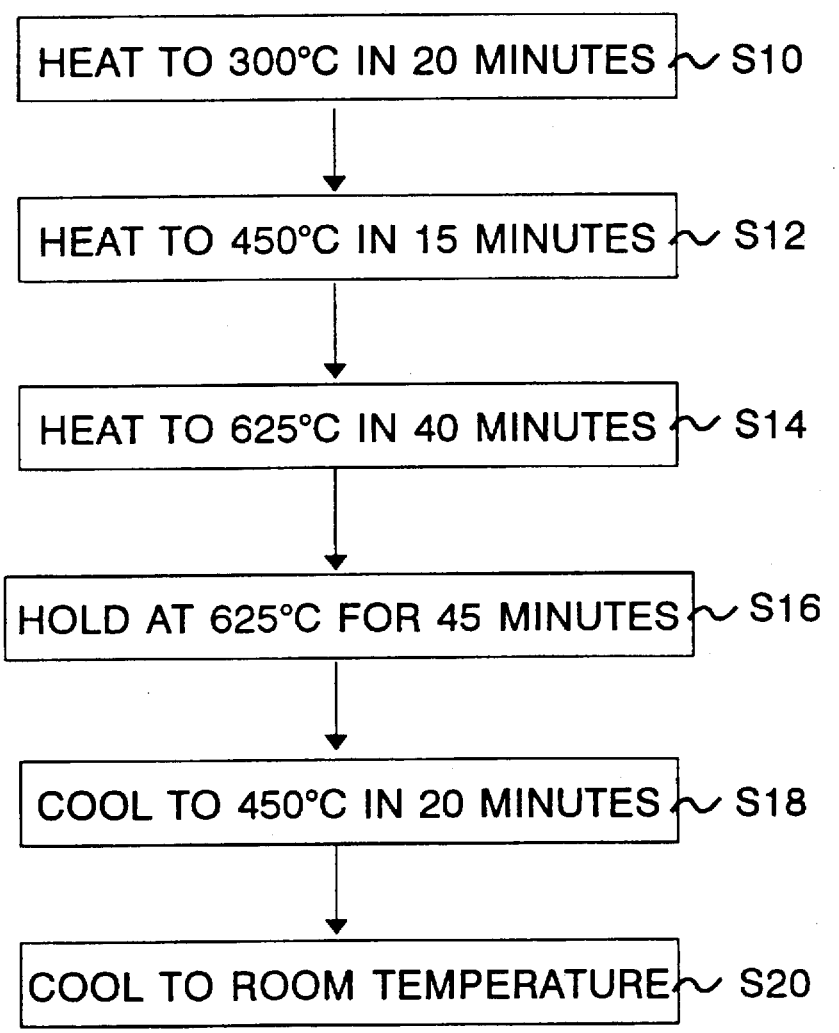
FIG. 2 is a flow chart describing a process of sintering the consolidated powders into an ingot of the metal matrix composite according to an embodiment of the present invention.

As shown in the flow chart of FIG. 2, the ingots are heated at step S10 from room temperature to 300° C. during a 20 minute ramp period to burn off binder and water. The ingots are then heated at step S12 to 450° C. during a 15 minute ramp period to burn off any remaining binder. Subsequently, the ingots are heated at step S14 to 625° C. during a 40 minute ramp period and held at 625° C. at step S16 for 45 minutes. During this time close grain boundaries are formed. The ingot is then cooled at step S18 from 625° C. to 450° C. in 20 minutes using a nitrogen gas backfill. Finally, at step S20 the ingots are cooled to room temperature at a rate less than or equal to 40° C. per minute using nitrogen gas. The resulting boron carbide-metal matrix composite material has a density ranging from approximately 2.5 to 2.8 g/cm$^3$ depending on the type of aluminum alloy used or whether aluminum is used for the metal matrix material.

A typical relative weight contribution of the boron carbide powder and aluminum or aluminum alloy metal matrix powder is approximately 10 to 60% boron carbide and 40 to 90% metal matrix. Several typical formulations of boron carbide-metal matrix composites according to the present invention are described below:

1. A metal matrix composite of aluminum alloy 6061 metal matrix and 20 weight % boron carbide. This composite is weldable, castable, and extrudable and exhibits a tensile strength of approximately 65 kpsi and a yield strength of approximately 60 kpsi.

2. A metal matrix composite of aluminum alloy 7091 metal matrix and 20 weight % boron carbide. This material is weldable, castable, and extrudable and exhibits a tensile strength of approximately 100 kpsi and a yield strength of approximately 90 kpsi.

3. A metal matrix composite of aluminum alloy 6061 metal matrix and 30 weight % boron carbide. This composite is castable and extrudable and exhibits a tensile strength of approximately 60 kpsi and a yield strength of approximately 60 kpsi.

4. A metal matrix composite of aluminum alloy 7091 metal matrix and 30 weight % boron carbide. This material is castable and extrudable and exhibits a tensile strength of approximately 105 kpsi and a yield strength of approximately 100 kpsi.

Unlike other metal matrix composites containing silicon carbide and aluminum, the metal matrix composite of the present invention is readily weldable. During welding, silicon carbide and aluminum react to form aluminum carbide particles, which are brittle and tend to segregate at the weld joint, thus weakening the weld joint by their presence and by locally depleting the metal matrix composite of silicon carbide. The metal matrix composite of the present invention, however, does not have these problems. The boron carbide particulates coated with the metal additives described hereinabove tend to flux and move into the weld pool resulting in a very strong weld joint. Because boron carbide particulates have a melting point of about 2450° C., the boron carbide is chemically inert at aluminum processing temperatures.

Figure 3:
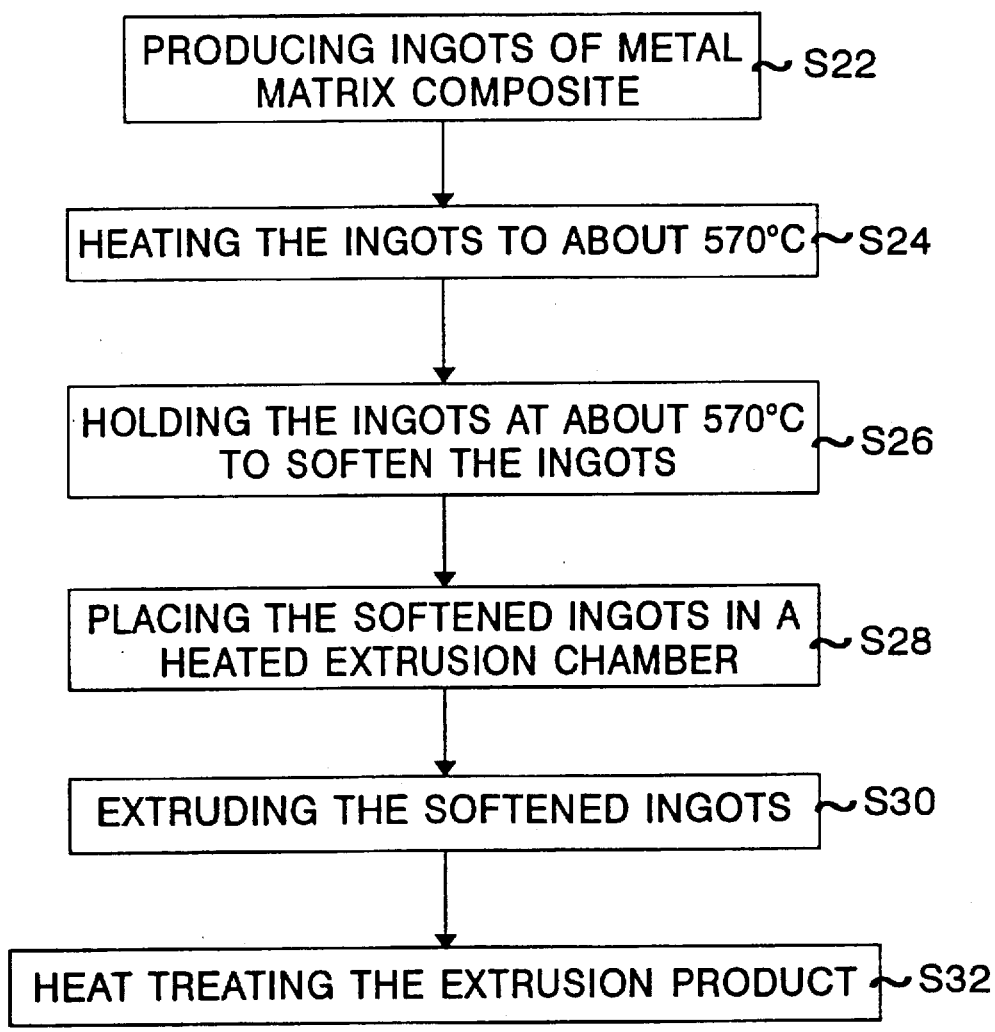
FIG. 3 is a flow chart describing an extrusion process for metal matrix composites according to an embodiment of the present invention.

Extrusion of boron carbide-metal matrix composites, as described in FIG. 3, begins by machining ingots of the composite at step S22 to a desired diameter for extrusion, which is generally between about 3.5 to 7 inches. The ingots are then heated at step S24 to a temperature of about 565° C. to 575° C., which is a softening temperature below the melting temperature of the composite. The heating can be performed as a two-step process where the ingots are first heated to a temperature of about 315° C. in a low-temperature furnace and then transferred to a high-temperature furnace and subsequently heated to a temperature of about 565° C. to 575° C. Preferably, the ingots are held at 565° C. to 575° C. at step S26 for at least one hour. The softened ingots are then transferred at step S28 to an extrusion chamber set at a temperature of about 490° C. Preferably, the extrusion chamber is heated by induction coils and the temperature of the extrusion chamber is monitored and controlled with an automatic temperature controller. Extrusion pressures can vary depending on the desired extrusion dimensions. Typically, the pressures used for extruding boron carbide-aluminum alloy metal matrix composites are about 15% to 20% greater than pressures used to extrude conventional aluminum alloys. For example, a 3.5-inch diameter ingot of boron carbide-metal matrix composite is extruded at step S30 at a peak or break-out pressure of about 3500 psi and a steady-state extrusion pressure of about 3000 psi. The speed of the extrusion ram is about 3.5 inches/minute for a typical 3.5-inch diameter ingot. The average exit speed of the extrusion is about 15 to 30 feet/minute, depending on the size of the extrusion, and the exit temperature of the extrusion is about 10° C. lower than the temperature of the extrusion chamber.

The extruded boron carbide-aluminum alloy metal matrix composite of the present invention is preferably heat treated at step S32 using a T6-type schedule, which typically includes 2 hours at 530° C., a cold water quench, and aging for 10 hours at 175° C. Preferably, all welding is done before heat treatment.

Although the composite may be extruded in conventional dies, it has been found that for maximum die insert life, a die material made of titanium diboride is preferred. The titanium diboride die material is preferably hot pressed and then machined to an appropriate size. A small amount of boron carbide may be used to increase the hardness of the die. Typically, the die is made of 99.5% pure titanium diboride in an amount equal to about 92 to 98% by weight, with the remaining fraction being 99.5% pure boron carbide having a particulate size less than about 10 μm.

Figure 4:
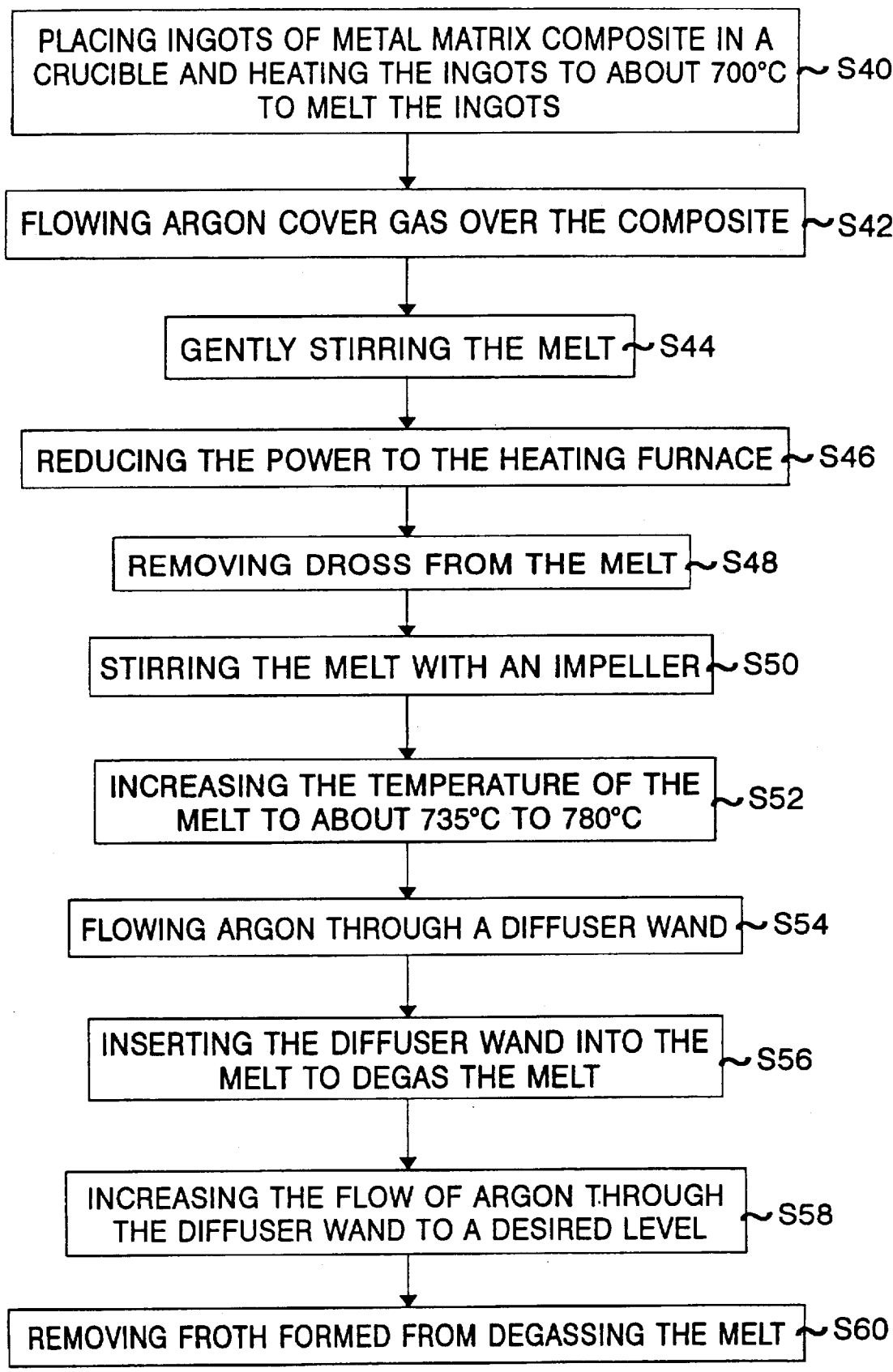
FIG. 4 is a flow chart describing a casting process for metal matrix composites according to an embodiment of the present invention.
Figure 5:
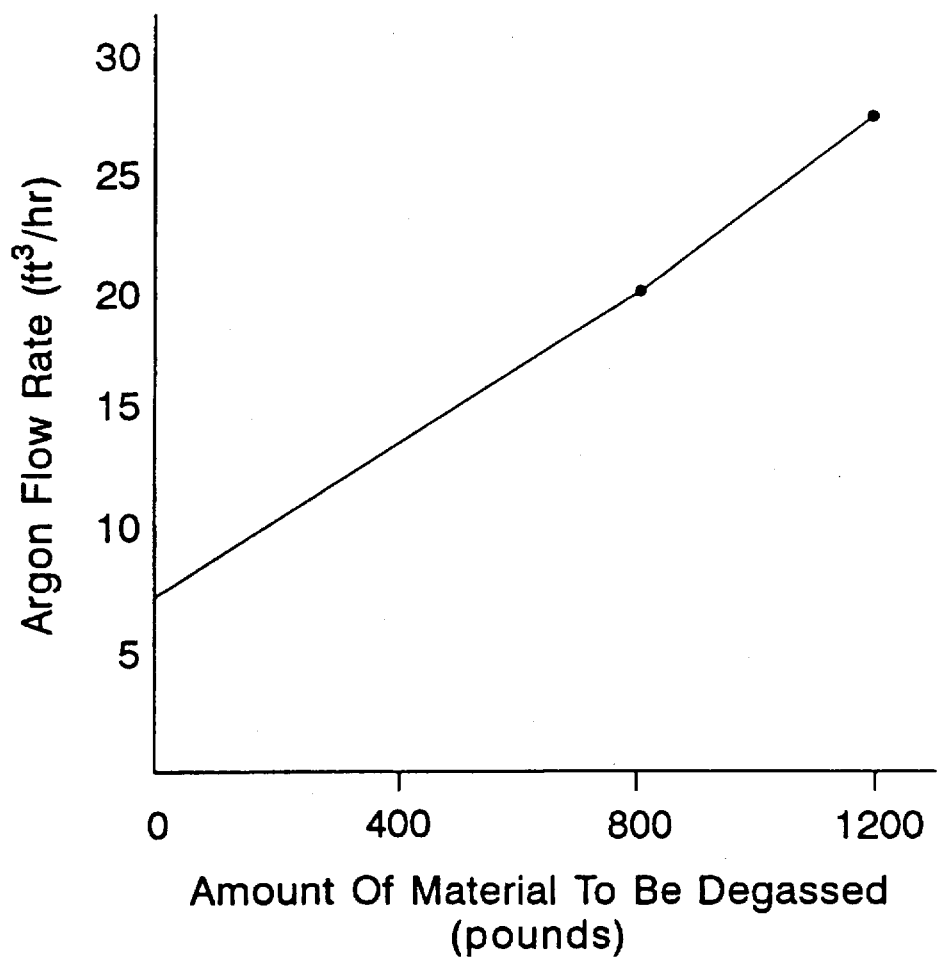
FIG. 5 is a degassing chart used for the casting process described in FIG. 4.

In casting a boron carbide-aluminum alloy metal matrix composite, as described in FIG. 4, ingots of the composite are placed in a crucible which is then put into a furnace that is initially at a temperature between room temperature and a moderately warm temperature of about 260° C. The ingots should be free of dirt and moisture. The ingots are then heated to about 700° C. at step S40. If the furnace includes dual temperature controls, the interior temperature controller preferably is set at about 700° C. and the exterior temperature controller preferably is set at 800° C. or above. If desired, at step S42 a cover gas of argon flowing at a rate of about 10 liters/minute can be used. As the composite in the crucible softens and melts, additional ingots may be added to the crucible. Once the ingots are completely molten, the melt is gently stirred in the crucible at step S44. Preferably, the gentle stirring is done with a dry, preheated paddle. As the melt reaches a temperature of about 675° C., the power to the furnace is reduced at step S46 to avoid overshooting the desired temperature of 700° C. Preferably, it should take at least 30 minutes for the temperature of the melt to increase from 675° C. to 700° C. During this time, dross will rise to the surface of the melt. This dross is skimmed off and discarded at step S48. The amount of dross that forms is typically about 2% to 5% by weight of the melt, but this amount may vary depending on the cleanliness of the ingots used. After removing the dross, the melt is stirred with an impeller at step S50 that has been preheated to a temperature of at least 200° C. to ensure that it is free of moisture. Preferably, the impeller is inserted into the melt at an angle of about 15° to 30° from vertical. The impeller is operated at a location about 4 to 6 inches from the bottom of the crucible. If a shaft is used to extend the impeller into the melt, the shaft should be made of graphite and should not be made of steel. The impeller speed is typically about 250 to 400 rpm, which is sufficient to cause a strong stirring movement in the melt without creating a vortex. After about 15 minutes of stirring with the impeller, the melt temperature is increased to about 735° C. to 780° C. at step S52 and then degassed. An argon diffuser wand made of graphite or a ceramic composite is used to degas the melt. A flow of dry argon having less than 3 ppm water vapor is established in the diffuser wand at step S54. Initially, the flow rate is about half the suggested flow rate for the amount of molten composite in the crucible. FIG. 5 shows the suggested argon flow rate as a function of the amount of molten composite to be degassed. The argon diffuser wand is slowly immersed into the melt at step S56 so that the end of the wand is at a level below the end of the impeller. Note that during insertion of the diffuser wand, the impeller is temporarily stopped for safety reasons. After the diffuser wand is properly positioned, the impeller is restarted and the flow of argon through the diffuser wand is increased at step S58 to the desired level as prescribed in FIG. 5. The injection of argon into the melt will cause a froth of stable bubbles to form at the surface of the melt. This froth is continuously skimmed off and discarded at step S60. The amount of dross that forms is typically about 2% to 5% by weight of the melt. During degassing, it may be observed that a small orange flame occurs when surface bubbles break. This occurrence is caused by the presence of hydrogen in the bubbles and it demonstrates the effectiveness of the degassing operation. When the rate of froth formation is reduced and the melt gently bubbles around the diffuser wand, the melt is held at this condition for about 20 minutes before it is ready for casting.

The embodiments described above are illustrative examples of the present invention and it should not be construed that the present invention is limited to these particular embodiments. Various changes and modifications may be effected by one skilled in the art without departing from the spirit or scope of the invention as defined in the appended claims.

What is claimed is:

1. A method of extruding a boron carbide-aluminum alloy metal matrix composite comprising the steps of:
   producing ingots of boron carbide-aluminum alloy metal matrix composite having a desired diameter for extrusion, wherein the ingots are produced by a process that does not require melting of the aluminum alloy metal matrix material;
   heating the ingots to a softening temperature of about 570° C.;
   holding the ingots at about 570° C. for at least one hour to soften the ingots without melting the ingots; and
   extruding the softened ingots through an extrusion die with an extrusion ram operating at pressures that are approximately 15% to 20% greater than pressures used for extruding aluminum alloys to form an extrusion product.

2. A method of extruding according to claim 1, wherein the ingots are extruded in an extrusion chamber heated to a temperature below about 570° C.

3. A method of extruding according to claim 2, wherein the extrusion product has an exit temperature that is about 10° C. lower than a temperature of the extrusion chamber.

4. A method of extruding according to claim 1, wherein the extrusion die comprises hot pressed powders of titanium diboride and boron carbide.

5. A method of extruding according to claim 1, wherein the desired diameter of the ingots is 3.5 inches, the pressures used for extruding the ingots comprise a peak pressure of about 3500 psi and a steady-state pressure of about 3000 psi, the extrusion ram operates at a speed of about 3.5 inches/minute, and the extrusion product has an average exit speed of about 15 to 30 feet/minute.

6. A method of extruding according to claim 5, further comprising the step of heat treating the extrusion product by heating, quenching and aging.

7. A method of extruding according to claim 6, wherein the heat treating includes:
   heating to about 530° C. for about two hours;
   quenching in cold water; and
   aging at about 175° C. for about 10 hours.

8. A method of casting a boron carbide-aluminum alloy metal matrix composite comprising the steps of:
   mixing dry powders of boron carbide material and aluminum alloy metal matrix material to form a homogeneous mixture;
   compacting the mixture into solid ingots of the composite using pressure and heat;
   heating the ingots of the composite to about 700° C. to melt the ingots;
   gently stirring the melt while removing dross from the melt;
   impelling the melt to strongly stir the melt without forming a vortex in the melt;
   increasing the temperature of the melt to about 735° C. to 780° C.;
   flowing dry argon into the melt to degas the melt;
   continuously removing froth formed on the melt from degassing until the melt is degassed and a rate of froth formation is reduced and the melt gently bubbles; and
   cooling the melt to form a cast product.

9. A method of casting according to claim 8, wherein the impelling is at an angle of 15° to 30° from vertical.

10. A method of casting according to claim 8, wherein the impelling is at a speed of about 250 to 400 rpm.

11. A method of casting according to claim 8, wherein the impelling is continued for at least 20 minutes after the melt is degassed.

12. A method of casting according to claim 8, wherein the cooling is at a rate less than or equal to 40° C. per minute.

13. A method of casting according to claim 8, wherein the step of heating the ingots to 700° C. comprises controlling a heating rate when the temperature reaches 675° so that the temperature rises to 700° C. in over 30 minutes.

14. A method of casting according to claim 8, further including the step of flowing argon as a cover gas during heating.

* * * * *